US009089138B2

(12) United States Patent
Higgins et al.

(10) Patent No.: US 9,089,138 B2
(45) Date of Patent: Jul. 28, 2015

(54) ORGANOSILANE-NONIONIC WATER STABLE QUATERNARY AMMONIUM COMPOSITIONS AND METHODS

(76) Inventors: Thomas L. Higgins, Lattingtown, NY (US); Theodore Shlisky, Kings Park, NY (US)

( * ) Notice: Subject to any disclaimer, the term of this patent is extended or adjusted under 35 U.S.C. 154(b) by 0 days.

(21) Appl. No.: 12/529,883

(22) PCT Filed: Mar. 6, 2008

(86) PCT No.: PCT/US2008/056093
§ 371 (c)(1),
(2), (4) Date: Jan. 29, 2010

(87) PCT Pub. No.: WO2008/109775
PCT Pub. Date: Sep. 12, 2008

(65) Prior Publication Data
US 2010/0167613 A1    Jul. 1, 2010

Related U.S. Application Data

(60) Provisional application No. 60/905,379, filed on Mar. 7, 2007, provisional application No. 60/905,413, filed on Mar. 7, 2007.

(51) Int. Cl.
C11D 1/72 (2006.01)
C11D 9/36 (2006.01)
A01N 55/00 (2006.01)

(52) U.S. Cl.
CPC ..................................... A01N 55/00 (2013.01)

(58) Field of Classification Search
USPC ......... 510/276, 279, 287, 289, 343, 347, 356, 510/417, 421, 466
See application file for complete search history.

(56) References Cited

U.S. PATENT DOCUMENTS

| | | | |
|---|---|---|---|
| 4,842,766 A * | 6/1989 | Blehm et al. ..................... 516/23 |
| 4,967,758 A | 11/1990 | Masciarotte | |
| 5,013,459 A | 5/1991 | Gettings et al. | |
| 5,411,585 A * | 5/1995 | Avery et al. ................ 106/287.1 |
| 5,885,951 A * | 3/1999 | Loder ............................ 510/340 |
| 5,922,247 A | 7/1999 | Shoham et al. | |
| 5,959,014 A | 9/1999 | Liebeskind et al. | |
| 6,221,944 B1 | 4/2001 | Liebeskind et al. | |
| 6,451,755 B1 * | 9/2002 | Norman ........................ 510/466 |
| 6,632,805 B1 * | 10/2003 | Liebeskind et al. ............ 514/63 |
| 6,685,766 B2 | 2/2004 | Standke | |
| 6,706,842 B1 | 3/2004 | Duan | |
| 6,805,963 B2 | 10/2004 | Janssen et al. | |
| 6,972,148 B2 | 12/2005 | Janssen | |
| 6,994,890 B2 | 2/2006 | Ohlhausen et al. | |
| 7,244,420 B1 | 7/2007 | Samain | |
| 7,300,468 B2 | 11/2007 | Wright | |
| 7,335,234 B2 | 2/2008 | Jones | |
| 7,431,089 B1 | 10/2008 | Couillet | |
| 7,513,004 B2 | 4/2009 | Luckman | |
| 7,513,132 B2 | 4/2009 | Wright | |
| 7,534,304 B2 | 5/2009 | Conrad | |
| 7,585,426 B2 | 9/2009 | Collier et al. | |
| 7,589,054 B2 | 9/2009 | Ohlhausen et al. | |
| 7,695,524 B2 | 4/2010 | Wright | |
| 2002/0002125 A1 * | 1/2002 | Colurciello, Jr. et al. ...... 510/238 |
| 2002/0111282 A1 * | 8/2002 | Charaf et al. ................. 510/130 |
| 2003/0073600 A1 * | 4/2003 | Avery et al. .................. 510/382 |
| 2003/0109395 A1 * | 6/2003 | Neumiller ..................... 510/246 |
| 2006/0083772 A1 | 4/2006 | DeWitt et al. | |
| 2006/0094320 A1 | 5/2006 | Chen et al. | |
| 2006/0193816 A1 * | 8/2006 | Elfersy et al. ............. 424/70.28 |
| 2006/0281662 A1 * | 12/2006 | Cheung et al. ................ 510/504 |
| 2007/0013317 A1 | 1/2007 | Denes et al. | |
| 2007/0021383 A1 * | 1/2007 | Loder ............................. 514/63 |
| 2007/0065475 A1 * | 3/2007 | Elfersy ........................ 424/405 |
| 2007/0227557 A1 * | 10/2007 | Ohlhausen et al. ................ 134/4 |
| 2007/0237901 A1 | 10/2007 | Moses et al. | |
| 2009/0197786 A1 * | 8/2009 | Perry et al. .................... 510/191 |
| 2009/0223411 A1 * | 9/2009 | Higgins et al. ............... 106/287.1 |
| 2010/0028462 A1 * | 2/2010 | Bolkan et al. ................. 424/717 |
| 2010/0093666 A1 * | 4/2010 | Moses et al. .................... 514/63 |
| 2010/0235975 A1 * | 9/2010 | Cheung et al. .................... 4/222 |

* cited by examiner

*Primary Examiner* — Charles Boyer
(74) *Attorney, Agent, or Firm* — Sack IP Law p.c.; Alan M. Sack (57) ABSTRACT

Methods of applications of organosilanes optionally having a nonhydrolyzable organic group, but having one or more hydrolyzable groups, with a polyol containing at least three hydroxy groups, where any two of the hydroxy groups are separated by at least three intervening atoms by aerosolization of droplets between 0.5-8 microns are disclosed and an improved formulation comprising adding a nonionic wetting agent are disclosed. An improved aerosolization application technique and the improved formulation provide for smaller droplet size and better coverage of substrates to which the organosilanes are applied. The improved formulation has increased affinity, reduces surface tension and therefore can covalently bond more quickly. A method of treating a substrate, and the treated substrate so formed, by contacting the substrate with the improved formulation for a period of time sufficient for treatment of the substrate are disclosed.

29 Claims, 5 Drawing Sheets

NBAT 100 PTUS

ORGANOSILANE-NONIONIC WATER STABLE QUATERNARY AMMONIUM COMPOSITIONS AND METHODS

CROSS REFERENCE TO RELATED APPLICATIONS

This application claims the benefit of U.S. Provisional Patent Applications 60/905,379 filed Mar. 7, 2007 and 60/905,413 filed Mar. 7, 2007.

STATEMENT REGARDING FEDERALLY SPONSORED RESEARCH OR DEVELOPMENT

Not applicable.

TECHNICAL FIELD OF INVENTION

The invention relates to compositions employing organosilane compounds and their use as microbiocidal agents.

BACKGROUND OF THE INVENTION

Water stable organosilane compounds, products, and compositions for treating various substrates, articles treated with the compounds, products and compositions, and methods of treatment using the compounds, products and compositions are disclosed in U.S. Pat. Nos. 5,959,014, 6,221,944 and 6,632,805 to Liebeskind and Allred.

Improved compositions and methods employing these compounds are disclosed herein which provide advantages.

BRIEF DESCRIPTION OF THE DRAWINGS

In FIGS. 3-5, the numbers on the vertical axis represent an exponential value of the number ten. As such, 1.00E+00 is equivalent to $10^0$, or 1. 1.00E+01 equals $10^1$, or 10, and so on up to 1.00E+09, or $10^9$. On this axis is also "CFU", meaning "Colony Forming Units". In FIGS. 3 and 5, the horizontal axis represents the number of days over which the experiment was monitored.

In FIG. 4, the horizontal axis represents the number of hours over which the experiment was monitored.

DETAILED DESCRIPTION

Water stable organosilane compounds are described in U.S. Pat. Nos. 5,959,014, 6,221,944 and 6,632,805 which are herein incorporated by reference as if fully set forth in their entireties herein.

In one embodiment, it has been found that the compounds can be applied to various substrates via a spraying technique which reduces the size of the drops of the formulation to small micron size droplets such as 1-8 microns. This benefits the application process by minimizing labor, providing consistency and balance in the application process. The aerosolization spray technique can be done with deminimus labor force. In order to provide the droplets in the size preferred, an ultrasonic device for atomizing liquids is preferably employed, such as is disclosed in U.S. Pat. No. 5,922,247 which is herein incorporated by reference as if fully set forth herein. Other spraying or atomizing apparatuses can be used to achieve the droplet size preferred.

In another embodiment, it has been found that regardless of application technique, advantageous formulations employing these compounds can be made by adding a nonionic wetting agent to the previously described compounds and compositions. These formulations can be applied via the spraying technique described above in a particularly preferred embodiment, or via a number of other techniques. The formulation provides an advantage by allowing for more coverage of the substrate to be treated.

Figure 2A:
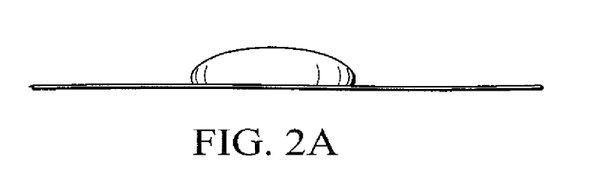
FIG. 2A depicts a side view of a single drop of the formulation of the invention depicted in FIG. 1A immediately after dropping onto a substrate.
Figure 2B:
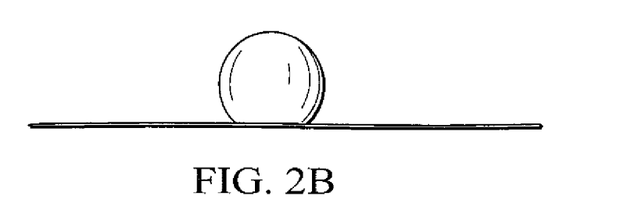
FIG. 2B depicts a side view of a single drop of a formulation depicted in FIG. 1B immediately after dropping onto a substrate.

The non-ionic wetting agent is employed to provide the characteristics of a facilitator to reduce surface tension and allow the composition to more rapidly penetrate the substrate or surface to be treated. By reducing the interfacial tension between the two media (the antimicrobial agent and the non-ionic) it will permit the combined formula to penetrate the surface more quickly while providing greater coverage on the surface. This phenomena is illustrated in FIG. 2A and FIG. 2B. FIG. 2A illustrates a droplet of a formulation comprising a non-ionic wetting agent while FIG. 2B illustrates a droplet without the wetting agent.

Suitable non-ionic wetting agents include ethoxylated alcohols; ethoxylated nonyl phenol(s); and ethoxylated alkyl phenol(s). When choosing a nonionic surfactant it is most preferred that the ethoxylation is between 9-12 moles to give the best wetting and detergency. Lower or higher ethoxylation reduces the surface tension properties and thus is not preferred although could provide some improved characteristics.

Preferably, the nonionic wetting agent is selected from the group consisting of: Ethoxylated Nonyl Phenol 9-12 moles, Ethoxylate, Ethoxylated Alcohol 9-12 moles and Ethoxylate, and Ethoxylated Alkyl Phenols 9-12 moles ethoxylate. Most preferably, the nonionic wetting agent is ethoxylated nonyl phenol 9-12 moles.

The compositions disclosed herein provide an advantage over previously described compositions in that they will better adhere to surfaces, including inert materials such as polypropylene and polystyrene. In addition, improved flow into crevices in surfaces is made possible. Another advantage is that the compositions disclosed herein allow for the formation of smaller droplets when using an aerosolization application method. The preferred application technique which allows for the smaller droplet size increases the affinity to certain surfaces and textiles, including materials composed of inert fibers. The surface tension is reduced and thus allows the formula to covalently bond more quickly. The compositions are non-toxic and so can be applied to surfaces, textiles and substrates in such exemplary industries as the healthcare and food and beverage industries without fear of harming humans either in contact with treated surfaces or who eat or handle food products.

Figure 1A:
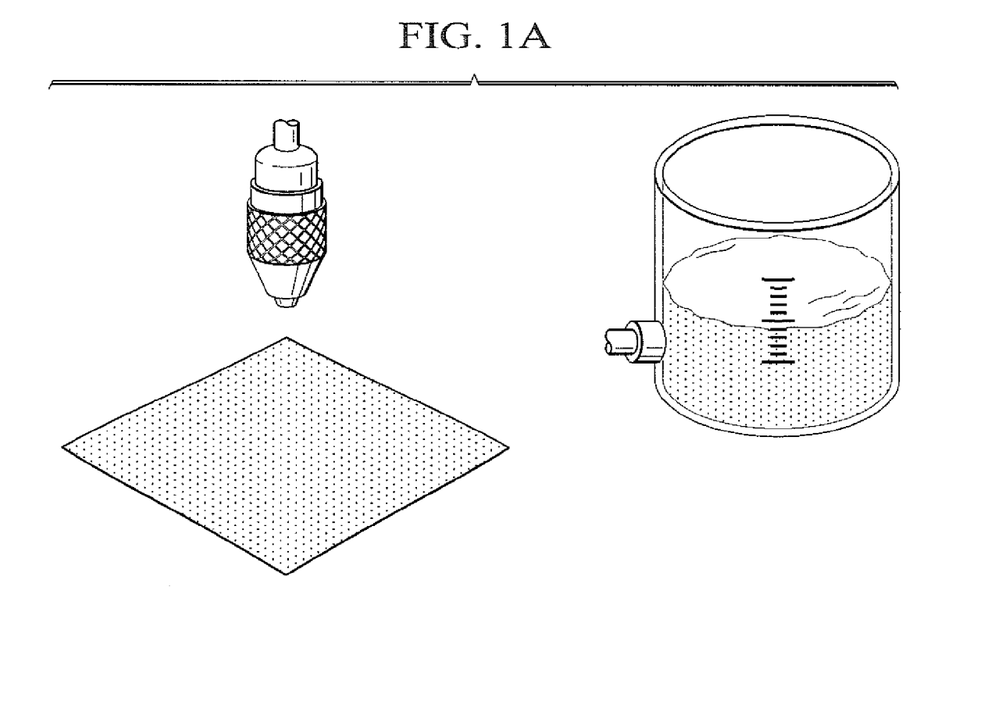
FIG. 1A depicts the use of a volume of a formulation of the invention for spray application to a substrate.
Figure 1B:
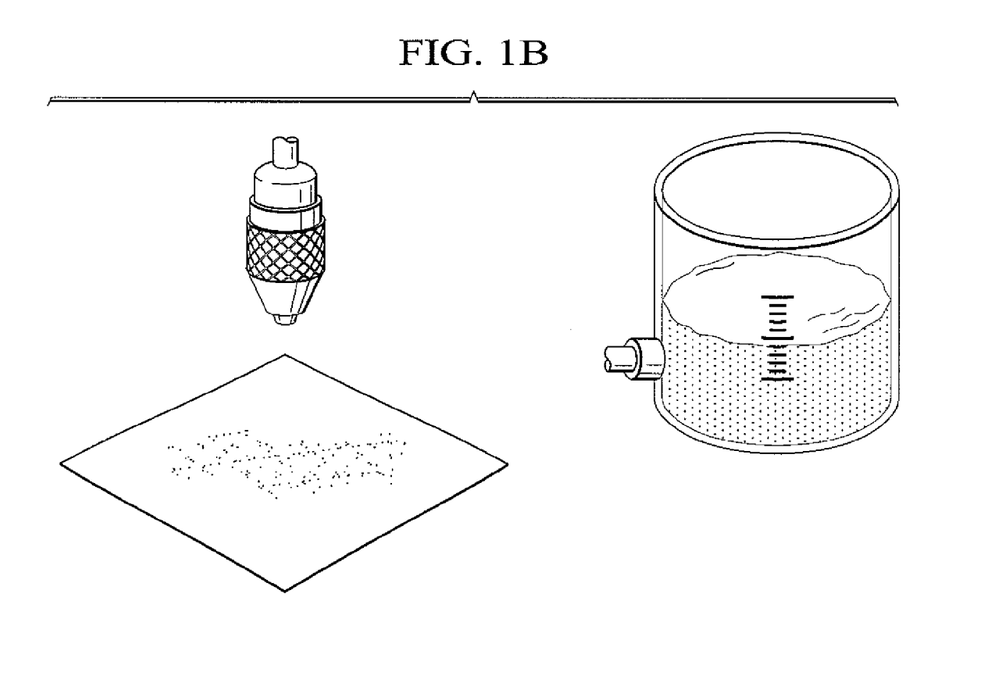
FIG. 1B depicts the use of an equal volume of a formulations not utilizing the disclosed invention in spray application to a substrate.

FIG. 1A and FIG. 1B show another advantage of using the formulation disclosed herein in combination with the preferred spraying technique. For the same volume, more coverage of a substrate can be achieved. FIG. 1A illustrates a substrate treated with the improved formulation containing the non-ionic wetting agent. The substrate is fully covered with the given quantity of liquid agent. FIG. 1B illustrates a substrate treated with a formulation which does not utilize the formulation of the invention. As can be seen, the same given quantity of liquid agent does not provide full coverage of the substrate. Therefore, more agent will have to be used to achieve full coverage. The nozzle in FIGS. 1A and 1B is representative of an aerosolization technique. Some improved coverage can be obtained with the formulation used in 1B over other techniques, but most preferred is using aerosolization (1-8 micron droplets, most preferably 0.5 to 5 micron droplets) in conjunction with the improved formulation of the invention.

The improved Organosilane-Non-Ionic Water Stabilized compositions can be made by first preparing an aqueous solution of water stable organosilane compounds (Solution A) pursuant to methodology disclosed in U.S. Pat. Nos. 5,959,014, 6,221,944 and 6,632,805 to Liebeskind and Allred.

A quantity of Solution A is then mixed with the selected non-ionic wetting agent and water necessary to make up the volume required. It is preferred that the invention can range from 0.5% of the active ingredient (3-trihydroxysilylpropyldimethyloctadectyl ammonium chloride) to 5.0% of the active ingredient in Solution A while proportionally maintaining the same percentage of the nonionic wetting agent(s) as would exist in the most preferred embodiment which is 90% Solution A with about 10% nonionic wetting agent tergitol NP-10 (Ethoxylated Nonyl Phenol 10 moles EO) and 0.5% D-Limonene (or without D-Limonene, wherein the 0.5% of such materials is replaced by an equal percentage of water) or other wetting agents disclosed as suitable herein.

Solution A, previously described by Liebeskind and Allred, supra, is improved by the addition of the disclosed non-ionic wetting agents in the proportions disclosed herein. The formula to be applied to selected surfaces can be better adapted to the application with employment of the present invention. The formula of the present invention results in creation of a smaller droplet size better able to penetrate hard and porous surfaces and textile materials and do to so more quickly. This provides better coverage, faster drying and greater efficacy.

Organosilane-Non-Ionic Water-stabilized composition is non-flammable and when stored in original, unopened containers has a minimum shelf life of 12-18 months from shipment.

Example 1

Henry Ford Hospital, Infectious Disease, Detroit, Mich. Summary of Fabric Test Conducted by Henry Ford Hospital System Using Solution A and 10% of Nonionic Agent The role of contaminated surfaces within the hospital environment is an area of infection control management that is difficult to control in both the laboratory and patient settings. Henry Ford wanted to evaluate the ability of an antimicrobial surfactant that permanently coats surfaces and fabric with covalently bound octadecyldimethylammonium ions (Solution A defined above) to reduce bacterial burden on contaminated surfaces. They also tested the ability of the product to inhibit growth of bacteria on fabric and surfaces in a patient room. In the fabric test they used the Solution A product and an extract of the formulation, the nonionic surfactant.

Methods: The fabric test was conducted according to the garment industry AATCC 100 protocol. Swatches of fabric were cut from a patient gown. Treated and untreated material was inoculated with *S. aureus*. Bacterial surveys were conducted over a 14 day period.

Overall Results: In the fabric test, Solution A with a 10% addition of the nonionic prevented the growth of *S. aureus* immediately upon contact and prevented growth for 14 days.

In the fabric test detailed below, Solution A with the 10% nonionic agent was successful in completely preventing the growth of *S. aureus*. In evaluating the product for its antimicrobial activity, they have demonstrated Solution A with the 10% nonionic agent has the potential to become an important component in infection control practices for textiles.

The fabric test was conducted according to the protocol set forth in AATCC 100. 2" circular swatches of fabric were cut from a patient gown consisting of a 50% cotton blend obtained from their Infectious Disease Clinic. All swatches were hand washed in luke warm water with Solution A with the 10% nonionic agent and allowed to completely air dry. Test swatches were treated with Solution A with the 10% nonionic agent by thoroughly soaking the fabric in the product. The material was then allowed to air dry completely before inoculation. Four stacked swatches of treated and untreated fabric were infected with 4 mL of *Staphylococcus aureus* at 0.5 McFarland. An additional control of untreated and uninfected material was established. Three different test conditions were conducted.

First Test Condition: The first condition collected bacterial samples from the fabric at time points 0, 24 h, 48 h and 72 h after initial inoculation. All swatches were washed between collections with Solution A and the nonionic agent and allowed to air dry. The fabric swatches were incubated for 24 h at 35° C. prior to the sampling. The samples were then aliquoted and incubated for 24 h at 35° C.

Second Test Condition: The second condition bacterial samples at 0, 24 h, 72 h and 96 h. Swatches were incubated at 35° C. for 24 h prior to sampling and washed between samplings as before. The samplings were then aliquoted and incubated for 48 h at 35° C.

Third Test Condition: The third condition collected bacterial samples at time points 0, 1 d, 7 d and 14 d without washing between samplings. Fabric was allowed to sit at room temperature and exposed to air for the time between samplings. The fabric was not incubated prior to sampling.

Sampling was conducted by placing each stack of four swatches in 100 mL of sterile saline and vigorously shaking for 1 minute. An aliquot of the saline was then removed and dilutions were prepared equivalent to $10^0$, $10^1$ and $10^2$. 100 uL from each dilution was plated as a lawn on to TSA blood plates and incubated at 35° C. without $CO^2$ for 18-24 h or 48 h depending on the condition. Resulting colonies were counted as appropriate.

In order to determine the impact of Solution A with the nonionic agent on treated fabric, a patient gown was retrieved from a clinical office and cut in to swatches for testing. The first experiment evaluated the product using *Staphylococcus aureus* ATCC strain 29213 as the inoculum. The fabric was sampled every 24 h post initial inoculation. Prior to sampling, the swatches were incubated at 35° C. for 24 h. The material was then washed and dried between sampling. Organisms were sampled from the fabric by vigorously shaking the material in sterile saline. Aliquots of the samples were then incubated for 24 h and growth of organism was assessed.

Figure 3:
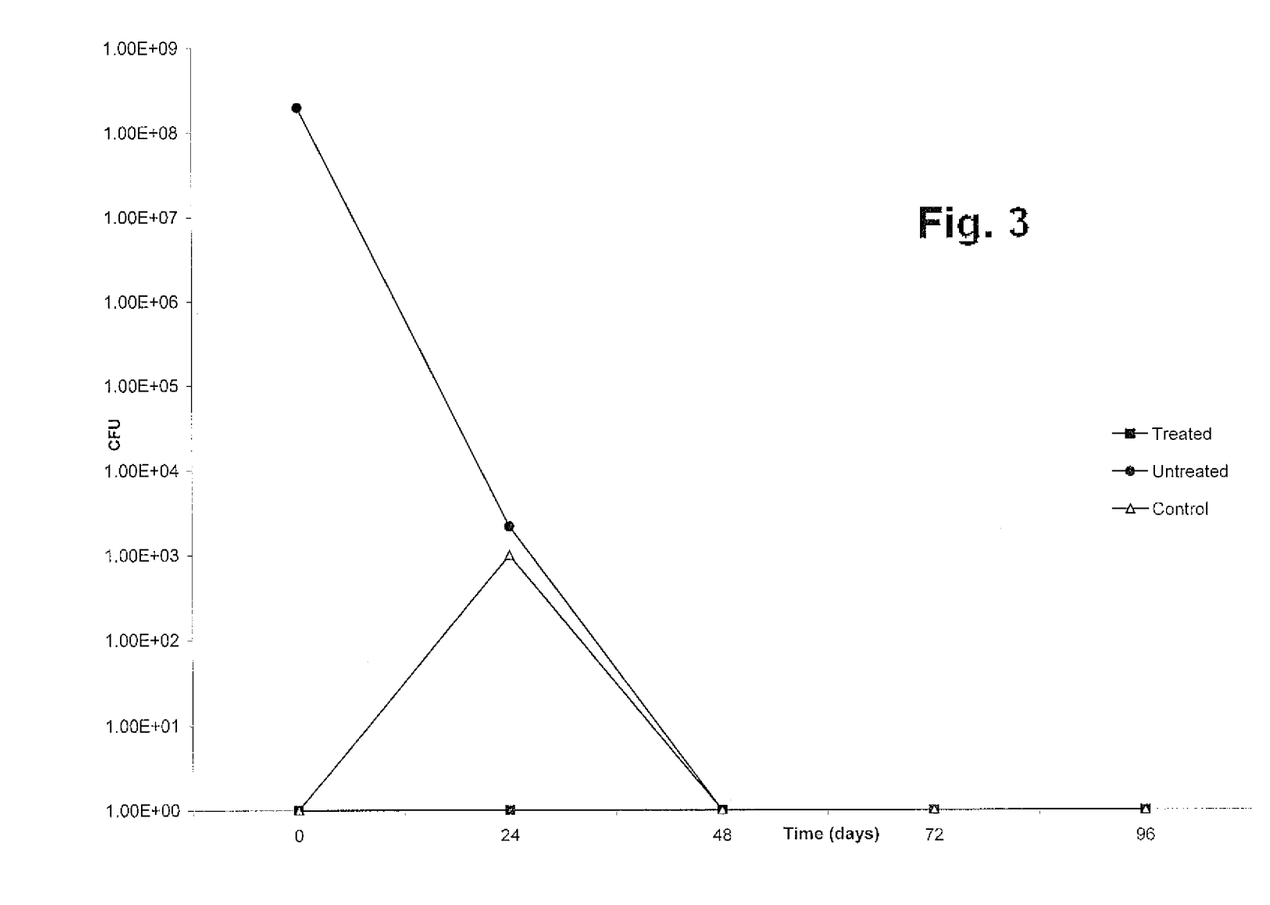
FIG. 3 is a graph showing the results of a fabric test comparing use of the formulation of the invention with 10% nonionic agent on fabric from a clinical gown inoculated with a known amount of Staphylococcus aureus bacteria incubated for 24 hours prior to testing for bacterial count at the intervals shown.

Referring to FIG. 3, in general *S. aureus* was applied to Solution A with the 10% nonionic agent treated and untreated material. Control fabric was untreated and not inoculated. Fabric was sampled every 24 h and aliquots were incubated at 35 C for 24 h.

As shown in FIG. 3, Solution A with the nonionic agent was able to reduce the bacterial burden on the fabric immediately after treatment. No growth was observed in any of the test swatches or controls after 48 h. This is presumed to be due to the efficiency of the Solution A with the nonionic agent used in the washing process. The spike observed in the control swatch was a contaminant and was not *S. aureus*.

Figure 4:
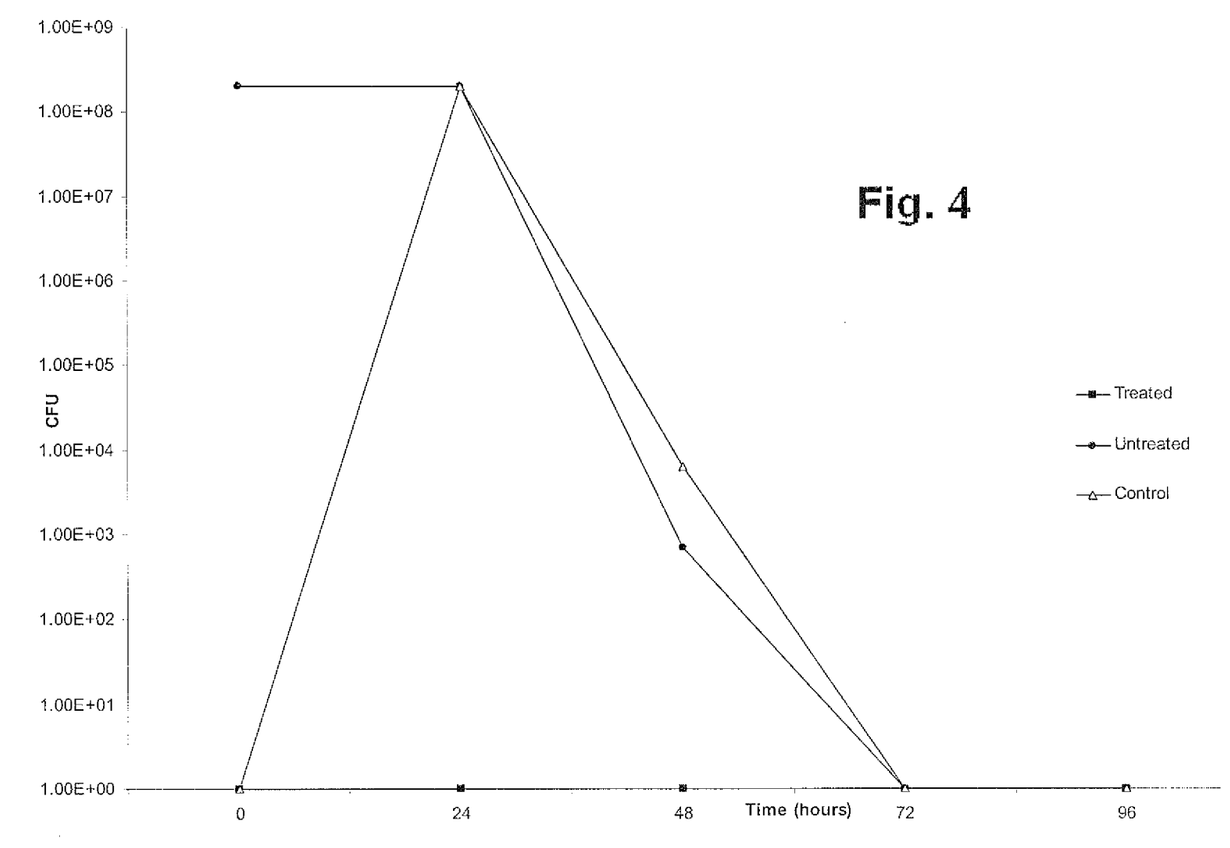
FIG. 4 is a graph, showing the results of a second fabric test comparing use of the formulation of the with the 10% nonionic agent treated and untreated material from a clinical gown inoculated with a known amount of Staphylococcus aureus bacteria incubated for 48 hours prior to testing for bacterial count at the intervals shown.

Now referring to FIG. 4, *S. aureus* was applied to Solution A with the 10% nonionic agent treated and untreated material. Control fabric was untreated and not inoculated. Fabric was sampled every 24 h and aliquots were incubated at 35 C for 48 h.

To determine if longer incubations were required to detect organism growth after the detergent washings, they sampled the fabric every 24 h as before, however they increased the incubation time of the aliquots to 48 h at 35° C. As before, the swatches were washed with detergent and dried between samplings. Swatches were also incubated at 35° C. between samplings. As shown in FIG. 4, a reduction in bacterial burden following the detergent washings was observed. Still, Solution A with the nonionic agent was able to immediately reduce the bacterial burden after the initial inoculation.

Under normal usage condition, patient gowns in their infectious disease (ID) Clinic would be more likely to be stored for several days to weeks before being used and since the last washing. In an effort to simulate a more real world application, fabric swatches were inoculated with *S. aureus* and then allowed to sit at room temperature exposed to air for 7 days. Swatches were not incubated prior to sampling. They also wanted to determine the effect of Solution A without the added activity of the nonionic.

Figure 5:
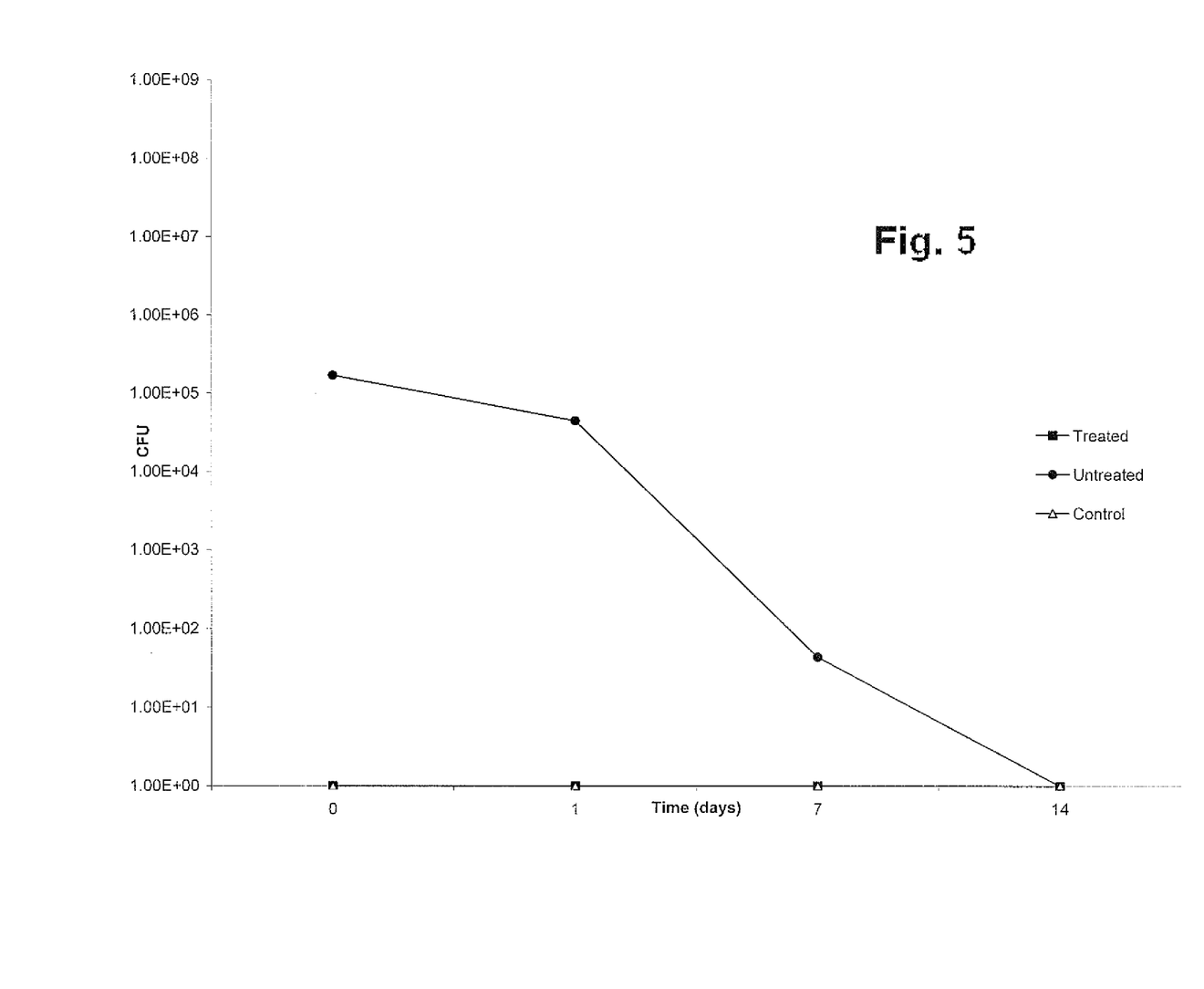
FIG. 5 is a graph showing the results of a third fabric test comparing use of the formulation of the invention with 10% nonionic agent treated and untreated material from a clinical gown inoculated with a known amount of Staphylococcus aureus bacteria incubated for 7 days at room temperature prior to testing for bacterial count at the intervals shown.

Now referring to FIG. 5. *S. aureus* was applied to Solution A with the 10% nonionic agent treated and untreated material. Control fabric was untreated and not inoculated. Fabric was sampled every 7 days and aliquots were incubated at 35 C for 48 h.

Therefore, the fabric was not washed between sampling periods. The results are displayed in FIG. 5. In this experiment, the untreated material was observed to have a much slower decay in the number of organisms recovered as compared with the previous conditions. This provides evidence that the nonionic was also beneficial in reducing bacterial burden over time. Taken together these data demonstrate that Solution A is efficient at preventing bacterial growth on contaminated fabric. Furthermore, a combination of Solution A with the nonionic agent provides satisfactory protection against contamination as an infection control measure.

Example 2

Another test was conducted at the Henry Ford Hospital System wherein Solution A containing 5% of the active ingredient was applied to a polypropylene material by spray method and fan dried, and the Organosilane-Non-Ionic Water Stabilized composition as described above was applied and dried in the same manner. Three samples of polypropylene material were provided for each test. Each material was cut into four equal parts. Two sections from each material were identified as replicates A and two were identified as replicates B. Replicates A were placed into each of three sterile culture containers. B replicates were also placed into each of three sterile culture containers for a total of six separate cultures. Each culture container held two material sections, one to be used for the 2 hour time point and one to be used for the 24 hour time point. The polypropylene material was either treated with 5% concentrated Solution A (Liebeskind and Allred), 4.5% Organosilane-Non-Ionic Water Stabilized composition, or left untreated.

A methicillin resistant *Staphylococcus aureus* patient isolate was grown overnight in a Muehler-Hinton liquid broth culture. Titer was determined by optical density and liquid culture was diluted to a concentration of $1 \times 10^7$ organisms per mL. Material in each culture container was inoculated with $5 \times 10^7$ organisms. All liquid was absorbed by the material, though total absorption took longer for dark blue and pink colored polypropylene materials used for the invention and control respectively in order to differentiate the experimental conditions more easily.

Materials were incubated at 35° C. without $CO_2$. At 2 hours, one material section from each of the six containers was selected and placed into sterile jars into which 100 mL of sterile saline was added. The jars were vigorously shaken for approximately 2 minutes. Aliquots of the saline solution were taken and dilutions were made for 100, 101 and 102. 100 microliters from each dilution was plated as a lawn on to TSA plates containing 5% sheep blood. Plates were incubated at 35° C. without $CO_2$ for 24 hours and colony forming units were enumerated. Plates were placed back into incubation for a further 24 hours for a total of 48 hours and colony forming units were enumerated again.

At 2, 24 and 48 hours post inoculation, the remaining materials sections were removed from each of the six containers and sampled as previously described. Results observed are tabulated in Table 1.

TABLE 1

|  | 2 h dilution | 24 h | 48 h | ave | 24 h dilution | 24 h | 48 h | ave |
|---|---|---|---|---|---|---|---|---|
| Mask untreated | | | | | | | | |
| rep A | 1 | TNC | TNC | | 1 | TNC | TNC | |
|  | 10 | TNC | TNC | | 10 | TNC | TNC | |
|  | 100 | 600 | TNC | | 100 | 1320 | TNC | |
| rep B | 1 | TNC | TNC | | 1 | TNC | TNC | |
|  | 10 | TNC | TNC | | 10 | TNC | TNC | |
|  | 100 | 1500 | TNC | 1050 | 100 | 1836 | TNC | 1578 |
| Solution A | | | | | | | | |
| rep A | 1 | 0 | 0 | | 1 | 0 | 0 | |
|  | 10 | 0 | 0 | | 10 | 0 | 0 | |
|  | 100 | 0 | 0 | | 100 | 0 | 0 | |
| rep B | 1 | 1972 | TNC | | 1 | 12 | 12 | |
|  | 10 | 271 | TNC | | 10 | 4 | 4 | 2 |
|  | 100 | 19 | 22 | 10 | 100 | 0 | 0 | |
| Organosilane-Non-Ionic Water Stabilized composition | | | | | | | | |
| rep A | 1 | 0 | 0 | | 1 | 0 | 0 | |
|  | 10 | 0 | 0 | | 10 | 0 | 0 | |
|  | 100 | 0 | 0 | | 100 | 0 | 0 | |
| rep B | 1 | 0 | 0 | | 1 | 0 | 0 | |

TABLE 1-continued

| | 2 h dilution | 24 h | 48 h | ave | 24 h dilution | 24 h | 48 h | ave |
|---|---|---|---|---|---|---|---|---|
| | 10 | 0 | 0 | | 10 | 0 | 0 | |
| | 100 | 0 | 0 | 0 | 100 | 0 | 0 | 0 |

TNC = too numerous to count

At the 2 hour evaluation, the 5% concentrated product (Solution A) resulted in a reduction in bacterial load of 99.05%. The material treated with the 4.5% Organosilane-Non-Ionic Water Stabilized composition resulted in a 100% reduction.

At the 24 hour evaluation, the 5% concentrated product (Solution A) reduced bacterial load by 99.99%. The material treated with the 4.5% Organosilane-Non-Ionic Water Stabilized composition resulted in a 100% reduction.

Reductions were calculated using the number of colonies obtained from blood plates after 24 hours of incubation.

This demonstrated several supporting advantages of the new inventions, those being better efficacy; excellent residual protection over 24 and 48 hours, better formula coverage on the material, and at the production and application stages smaller droplets, greater fabric adherence, quicker drying and greater surface penetration. Colonies were still detected in the test under all conditions, indicating the presence of live organisms which can replicate except with the fabric treated with the organosilane non-ionic water stabilized composition. The 100% effectiveness of the organosilane non-ionic water stabilized composition represents an improvement.

In various embodiments, surfaces and substrates treatable with the compositions, products and compositions of the invention solution include, but are not limited to, textiles, carpet, carpet backing, upholstery, clothing, sponges, plastics, metals, surgical dressings, masonry, silica, sand, alumina, aluminum chlorohydrate, titanium dioxide, calcium carbonate, wood, glass beads, containers, tiles, floors, curtains, marine products, tents, backpacks, roofing, siding, fencing, trim, insulation, wall-board, trash receptacles, outdoor gear, compressible and incompressible fluid filtration materials, water purification systems, and soil. Furthermore, articles treatable with the compounds, products and compositions of the invention include, but are not limited to, materials used for the manufacture thereof, aquarium filters, buffer pads, fiberfill for upholstery, fiberglass duckboard, underwear and outerwear apparel, polypropylene fabrics, filters and membranes, polyurethane and polyethylene foam, sand bags, tarpaulins, sails, ropes, shoes, socks, towels, disposal wipes, hosiery and intimate apparel, cosmetics, lotions, creams, ointments, disinfectant sanitizers, absorbents, wound dressings; micro-fibers; wood preservatives, plastics, adhesives, paints, pulp, paper, cooling water, and laundry additives and non-food or food contacting surfaces in general.

The composition can be sprayed, rolled, wiped, fogged, or applied by mopping to the article to be treated or can be exhausted or padded onto textile materials. It can also be processed through dipping, soaking, or roller pressure and heat setting processing. Choice of application and/or processing method depends upon the nature of the surface to be treated.

As previously stated, the composition can be advantageously used in an aerosolization spray techniques for certain surfaces or rooms with the spray comprising preferably small micron size droplets such as 1 to 8 microns, most preferably 0.5-5 microns. This benefits the application process by minimizing labor, providing consistency and balance in the application process. The aerosolization spray technique can be done with deminimus labor force.

Another advantageous application method is applying by 'wet-wipe' by first soaking the wipe, letting it remain moist in a container and then applying provides effective application and provides the surface with the desired prophylactic protection because by lowering the interfacial tension between the two media of the antimicrobial and the wetting agent, the resulting composition will play a key role in the removal of dirt from surfaces and textiles.

Example 3

Preparation of Organosilane-Non-Ionic Water-Stabilized Composition

A 5% W/V (weight/volume) aqueous solution of 3-(trimethoxysilyl)propyldimethyloctadecyl ammonium chloride was converted to 5% 3-(trihydroxysilyl)propyldimethyloctadecyl ammonium chloride, 0.8% 3-chloropropyltrimethoxysilane, and 1.9% pentaerythritol. (hereinafter "Solution A") pursuant to a method disclosed in U.S. Pat. No. 5,959,014. In brief, A 22 L reaction flask was charged with 6250 g. (21.0 Mol.) of dimethyloctadecylamine, 5844 g. (29.4 Mol.) of 3-chloropropyltrimethoxysilane, and 76 g. (0.84 Mol.) of trioxane. The mixture was heated to 140.degree. C. for 12 hours while stirring and was then cooled to 80.degree. C. 2 L of methanol was then added and the mixture was cooled to approximately 40.degree. C.

This mixture was then transferred to 171 L of water, into which 4000 g. of pentaerythritol had been previously dissolved. After thorough mixing the pH of the solution was checked. (If the pH is above 7.0 (basic) a small amount of HCl is added until the pH is below 7.0).

The mixture was then diluted to 209 L with additional water. The resulting solution contained approximately 5% 3-(trihydroxysilyl)propyldimethyloctadecyl ammonium chloride, 0.8% 3-chloropropyltrimethoxysilane, and 1.9% pentaerythritol. (hereinafter "Solution A")

To a quantity of Solution A (to equate to 90% of the final mixture), was added 10% of the nonionic Tergitol NP-10 (Ethoxylated Nonyl Phenol 10 moles EO) an amount to form the final mixture. After mixing, 0.5% of D-Limonene may be added. The final composition (an "Organosilane-Non-Ionic Water-stabilized Composition") exhibited improved adherence to a variety of surfaces.

Example 4

Processes for Textile Applications

By Exhaustion

Fabric should be dyed as usual, post scoured and neutralized. Alkalinity may prohibit Organosilane-Non-Ionic Water-stabilized compositions from attaching to fabric. The pH of the fabric should be less than 6.0 to aid exhaustion.

Set temperature at 110°-120° F.

Make up solution of Organosilane-Non-Ionic Water-stabilized composition in head tank or side tank of jet or dye bath equipment commonly found in textile facilities (or: Take solution of Organosilane-Non-Ionic Water-stabilized composition in the amount of 2%-4% of the weight of the goods to be laundered. (100 lbs. of textiles would use 3 lbs. of liquid concentrate or less than ½ gallon).

Weigh Organosilane-Non-Ionic Water-stabilized composition carefully and take the solution and pour it into a separate five gallon pale and mix with warm water (80°-90° F.) for ten minutes (10) to assure proper dispersion. Acetic Acid or Citric may be used to adjust pH if necessary.

Inject solution of water and Organosilane-Non-Ionic Water-stabilized composition into jet. Hold temperature at 110°-120° F. for fifteen to twenty minutes to provide adequate time for exhaustion.

At end of cycle time, drop water. No rinsing is required.

Organosilane-Non-Ionic Water-stabilized composition can be exhausted on in the softener bath. The compatibility of all softeners with Organosilane-Non-Ionic Water-stabilized composition prior to employing this method.

Application of Organosilane-Non-Ionic Water-stabilized composition can be checked by two means: Bromophenol Blue indicator-indicates the presence of Organosilane-Non-Ionic Water-stabilized composition by a blue cast. If no Organosilane-Non-Ionic Water-stabilized composition is present, no color will form. pHydron quaternary Test Strips QT-10 can be used to indicate the presence of a quaternary compound. These can be used to determine the effectiveness of the bath treatment. The strips can be used to test the bath by dipping the strip therein and one can read the amount of quaternary compound, if any, that has been left in the bath. As an added benefit, testing with the strips would determine if any anionic surfactant would be necessary to add to wastewater prior to release to city sewer. These test strips can be purchased from Fisher Scientific.

Fabric can then be dried according to conventional methods. It should be noted that the product will exhaust at low temperatures at the right pH. The procedures recommend that testing be done to insure proper application of the product which will cover the differences between liquor ratios in a paddle, jet, rotary or pad application To prevent the discoloration or yellowish of fabrics, for example in the textile industry, it is necessary to control the pH of the bath. Alkalinity may prohibit Organosilane-Non-Ionic Water-stabilized composition from attaching to fabric. The pH of fabric should be less than 5.5 to aid exhaustion. Different Acids can be used for this process. The most common used are acetic acid and citric acid.

The concentration will be determined by the original solution used. Organosilane-Non-Ionic Water-stabilized composition will work and keep white fabrics from discoloring when the pH is from 4.5 to 5.5. It will also, pad or exhaust better when the pH is below 6.0. pH can be determined with a standard pH-meter or test strips.

By Padding

Fabric should be previously scoured and/or dyed and neutralized. Alkalinity may prohibit Organosilane-Non-Ionic Water-stabilized composition from attaching to fabric. The pH of the fabric should be less than 6.0 to aid pick up.

Determine an accurate wet pick up. It is preferable that fabric be padded wet or dry. However, if wet on wet finishing is necessary, it is imperative than an accurate exchange rate be calculated to effect enough Organosilane-Non-Ionic Water-stabilized composition to fabric.

Make up solution of Organosilane-Non-Ionic Water-stabilized composition in head tank or side tank near pad (Organosilane-Non-Ionic Water-stabilized composition solution and the amount of Organosilane-Non-Ionic Water-stabilized composition will be 1%-4% on the weight of the goods).

Calculate amount needed adjusting for wet pick up of fabric being padded. If vacuuming is used, make adjustment for this also.

Weigh Organosilane-Non-Ionic Water-stabilized composition carefully and accurately into warm water (80°-90° F.) Blend for 10 minutes to assure Organosilane-Non-Ionic Water-stabilized composition is adequately dispersed in water.

Drop solution to pad and run fabric through pad.

Check a wet pick up during run to assure Organosilane-Non-Ionic Water-stabilized composition is being affected to fabric.

Organosilane-Non-Ionic Water-stabilized composition can be padded on in the softener bath. Check compatibility of all softeners with Organosilane-Non-Ionic Water-stabilized composition prior to tying this.

Fabric can be dried according to conventional methods.

Application of Organosilane-Non-Ionic Water-stabilized composition can be checked by two means: Bromophenol Blue indicator-indicates the presence of Organosilane-Non-Ionic Water-stabilized compound by a blue cast. If no Organosilane-Non-Ionic Water-stabilized compound is present, no color will form. pHydron quaternary Test Strips QT-10- indicate the presence of a quaternary compound. These can be used to determine the effectiveness of the bath treatment. The strips can be used to test the bath by dipping the strip therein and one can read the amount of quaternary compound, if any, that has been left in the bath. As an added benefit, testing with the strips would determine if any anionic surfactant would be necessary to add to wastewater prior to release to city sewer. These test strips can be purchased from Fisher Scientific.

To prevent the discoloration or yellowish of fabrics, for example in the textile industry, it is necessary to control the pH of the bath. Alkalinity may prohibit Organosilane-Non-Ionic Water-stabilized composition from attaching to fabric. The pH of fabric should be less than 5.5 to aid exhaustion. Different Acids can be used for this process. The most common used are acetic acid and citric acid.

The concentration will be determined by the original solution used. Organosilane-Non-Ionic Water-stabilized composition will work and keep white fabrics from discoloring when the pH is from 4.5 to 5.5. It will also, pad or exhaust better when the pH is below 6.0. pH can be determined with a standard pH-meter or test strips.

By Spraying

On certain textiles, filters, membrane, nano and micro-fiber materials and non-woven extruded fabrics all pre-made, the formulation comprising material (Organosilane-Non-Ionic Water-stabilized composition) can be sprayed on in dilutions levels of 0.05%-4.5% of the active ingredient with conventional trigger spraying equipment, by aerosolization fogging [mist] spray, or by singular or multiple overhead nozzle spray releasers. Textiles can be hung after cleaning, and then spray on all sides, permitting the textile to either air dry or be processed through heat chamber or commercial dryer at less than 210° F. In certain instances of non-woven materials, the formula can be applied by spray, automatic sprayer or aerosolization spray release method, with preferable micron droplets of less than 6 in size, and air dried with a fan or processed through a heat chamber.

Healthcare Applications

Example 5

Medically Related Substrates

Organosilane-Non-Ionic Water-stabilized compounds described above can be effectively employed in the healthcare industry. Most preferably, the formulations taught herein employing the non-ionic wetting agent are employed. Examples of suitable locations and medical substrates where said compounds would be useful are healthcare facilities: hospitals, nursing homes, physician, dental and veterinary offices and operatories, waiting rooms, laboratories, and laboratory equipment, ambulatory clinics; "clean-rooms" and ambulances, patient transportation vehicles, computer keyboards, telephones, out-patient facilities; warehouse rooms in such facilities; including floors, walls, ceilings, door knobs, water and air-filtration systems; all air and arid duct systems, all bathrooms; showers; shower stalls and glass, and synthetic shower door coverings; shower faucets and drain covers; all tiles and adhesive fillers; laminates and finishes including alkyd, urethane, enamel, epoxy, siloxaline, amino resins, textile coatings, extrusion coatings, architectural coatings and overlays, anti-corrosion coatings, fire-resistant coatings, aliphatic coatings, vinyl-ester and polyester coatings, gel coatings, amino resins, resins used as additive mixes for cement, epoxy laminating resins, and blends and copolymers thereof; oncology departments; epidemiology departments; operating and recovery rooms; storage areas; elevators and stair wells, hand rails and buttons; soap dispensers and tabs; towel dispensers and tabs and pulls; toilet seats and covers; stalls, sinks and faucets; mirrors and windows, drapes and curtains; bed curtains and privacy curtains of all textile materials, woven, knitted and non-woven constructions; all beddings and sheets and pillow case of all textile materials and fiber and/or micro-fiber constructions, whether woven, non-woven or combinations of both, as well as all knitted materials used separately or in combination with woven and non-woven materials; body bags or bio-barrier body coverings; bed pads and absorbents; bed rails, and backs; table chairs and other furniture used within these facilities whether made of wood, wood by-products, or metals including but not limited to steel of all varieties; all furniture of extruded polymers of synthetic origins including but not limited to plastics; all floor coverings including synthetic tiles; ceramic tiles; wood, cement, concrete; carpeting of all fiber constructions All desk, computer key boards, mouse; phones; remotes, ear and head sets. In addition, medical equipment designed to contact a patient and take readings, including digital transmission surfaces.

Organosilane-Non-Ionic Water-stabilized compounds disclosed in Liebeskind and Allred as described above, and most preferably the formulations taught herein which employ the non-ionic wetting agent can be used to treat filters, including but not limited to air filters for furnaces, air-conditioners, air purification devices, automobiles, re-circulating air handling systems, air filters/materials); water filters; all materials consisting in the composition of such filter materials like carbon based filters; polypropylene and cellulose fibers, nano and micro-fibers, and all membrane materials used for filtration included but not limited to such materials and fibers.

These compounds and formulations can be employed in the treatment of blood filtration material consisting of but not limited to polypropylene, polystyrene; polyethylene, membrane and nano micro-fibers, resin materials used and treated with the formula to be incorporated into such filters; kidney filtration and blood filtration.

Further applications are the treatment of treat textiles used in the healthcare industry made of woven, non-woven, knitted and knitted and woven and nonwoven, nano and micro-fiber compositions, of fibers including but not limited to rayon, polyester, silk, nitril, polypropylene, polyolefin; polystyrene; polyethylene, cotton, linen, cotton and nylon blends, cotton and polyester blends, raime and nano and micro-fibers. Examples of such textiles are uniforms; linens; beddings; operating gowns; gloves used in the medical field; foot gear, such as disposable hospital slippers; towels; privacy curtains; body bags [as bio-barriers]; absorbents, woven and non-woven; socks; head gear; masks; face and eye protectors; disposable single-use blood cuffs; privacy curtains; foot coverings; sterile equipment blankets of woven; non-woven; knitted and combinations of knitted and woven and non-woven constructions including but not limited to cotton; cotton blends; polypropylene; polyester and polyester and cotton blends; nylon and nylon and cotton blends; rayon and rayon and cotton blends; silk; ramie; nano and micro fiber materials of synthetic and natural origins fibers whether woven or non woven, knitted or combination of knitted and woven or non-woven, wool and wool blended fabrics and fibers. It is appropriate for the aforesaid material whether woven, knitted, non-woven, brushed, fleeced, or sheared. It also may be used to treat gauze and band-aid dressing as well as wound-dressing materials The above-described compounds and formulations can be used to treat dry and wet wipes of woven; non-woven, knitted or combinations thereof, pre-moistened towelettes and tissue wipes, institutional sponges and mops, water pails, and squeegee rollers, mop handles, and vacuum cleaner bags, disposable plastic garbage bags and bed bags of all sizes and on all synthetic compositions.

The above-described compounds and formulations can be used to treat the interior and exterior of ambulances, carts, gurneys, stretchers, blankets, warming devices, stabilizing accessories, intravenous (i.v.) pole materials whether synthetic or metallic, IV lead wires; EKG lead wires and all bases, and tubing thereof. It can also be used to treat bed pans, trays, wheelchairs, machined mechanical components for assembly into final products, Endoscope sterilizers and disinfectors and associated equipment, Central supply shelving and counter tops, stethoscopes, metallic and synthetic derivatives, blood pressure cuff and single use disposable blood pressure cuffs, band-aids, gauze, wound dressing bandages, and catheters; stints; all assay equipment and materials used in the manufacture of such; skin grafts and synthetic skin grafts and protective covers, endoscopes, and other surgical apparatus, EKG wires and skin tabs, and for sterilizing garbage disposable bags, medical gloves of all synthetic material compositions (such as nitril, polypropylene and polystyrene) and finger tip coverings made of a variety of materials including but not limited to latex or nitril. Furthermore it has applications to periodontal uses such including but not limited paste, liquids, creams or ointments.

The above-described compounds and formulations also have application in emergency vehicles, homes, offices, automobiles, all transportation vehicles; hospitals and contagious illness rooms, hotels, schools, day care centers, and correctional facilities.

Agribusiness Applications

In addition to the health care industry, the above-described compounds and formulations have application in agribusiness for bacterial control in the raising of and processing of meat-producing animals, including poultry, swine, cattle, fish etc. They can also be used on plants and plant materials and derivatives. Example 6 concerns the poultry industry applications, but many of the same principals apply to the raising and processing of other meat producing animals. Example 7 provides an example of the use in plant agriculture.

Example 6

Poultry Industry Applications

The above-described compounds and formulations compositions can be used in the poultry industry. Spraying, fogging, mist, brushing, dipping, soaking, ultrasonic aerosolization, etc, can be employed to apply this solution to areas used to raise animals, meat processing areas, and to the animals themselves. For cleaning and disinfecting commercial applications, the above-described compounds and formulations can be used on livestock houses including cages and equipment, farm and transportation vehicles for animals, foot and tire dips, food processing plants (walls, ceilings, floors & fixtures), refrigerators and coolers, hatcheries (hatchers, setters, evaporative coolers, humidifying systems, cooling towers, ceiling fans, etc.) ability to protect pedigree eggs during collection, storage and incubation.

Brooder houses, laying houses, and equipment may be treated as follows. After houses and equipment are thoroughly cleaned, washed down and allowed to dry—and before a new flock is housed—the entire inside surface of the room (building) and all the equipment are sprayed with the proper concentration of the above-described compounds and formulations compositions and let dry before rehousing.

For example, the above-described compounds and formulations can be applied via spraying, fogging, mopping or rollers. Aerosol spray at different droplet sizes ranging from one-8 micron can be employed.

Application to and stainless steel equipment or processing machines by re-treating with an aminodiacetic acid for highly buffed stainless steel may be employed. Liquid aminodiacetic acid is first applied to the surface or stainless steel permitted to dry and then the above-described compounds and formulations compositions is applied, adhering to the acid instead of the actual metal.

Hatcheries (hatchers, setters, evaporative coolers, humidifying systems, ceiling fans, etc.) can be treated with the above-described compounds and formulations Chick hatcheries are thoroughly cleaned, washed downed, and disinfected after each hatch. The above-described compounds and formulations may be used to treat these areas and has the advantage of being long-lasting in that it does not need to be applied after every cleaning and wash down as it has residual activity in killing threatening bacteria or viruses before it is scheduled for the next application. An application schedule can be determined by periodic microbial testing using standard methods.

Egg Holding, Cooling and Storage Rooms can be treated with the above-described compounds and formulations. These facilities are air cooled and usually equipped with humidifiers connected to automatic controls. The above-described compounds and can be mixed with the humidifier spray and will add a controlling factor to kill *salmonella* or other harmful bacteria that might be on the surface of the eggs, cases, holding racks and room's interior surfaces.

Egg Breaking and Processing Rooms and Equipment can be treated with the above-described compounds and formulations compositions. Work rooms and equipment are thoroughly cleaned, washed downed and disinfected at the end of each day. Non-Ionic Microbiostatic Agent can be applied by a cleaning crew after one of the cleanings. The cleaning crew does not need to reapply the organosilane-non-Ionic-water-stabilized compositions after each cleaning since it continues to exhibit antibacterial activity.

Broiler Processing and Further Processing Operations can be treated as described above.

Other poultry application examples include application to feed packaging material and food storage bins to mitigate mold and fungi, poultry houses including cages and equipment, application to synthetic fingers (the synthetic like cork screws that beat off the feathers), walls, ceilings, crates, and filters, farm and transportation vehicles for animals (it will not damage brake linings of the vehicles and it is non-corrosive); foot and tire dips, processing Plants (walls, ceilings, floors & fixtures), refrigerators and coolers, conveyors belts of synthetic and natural based fibers in woven and non-woven constructions, and textiles worn or employed by poultry workers (e.g., uniforms, towels, masks, hats, shoes).

It can be applied to packaging as it will not leach off the surface, yet will kill the organisms which are encapsulated in the packaging, but not limited to trays, napkins inserts and clear package covering, those providing a longer shelf life. It can be applied to the egg shell, which would create a lattice prophylactic against environmental contaminants. This could also have utility in the pharmaceutical industry in the use of eggs for developing vaccines. It can be used on textiles used as bio-barrier to cover and protect vegetable, fruit and plant growth.

Example 7

Plant Applications

The Organosilane-Non-Ionic-Water-stabilized compositions disclosed in Liebeskind and Allred and the formulations thereof disclosed herein can be used on seedlings, on feed- and fertilizer storage bins and packaging materials to mitigate microbial growth therein. It can be sprayed on stems and leaves as well as fruits and vegetables.

The above-described compounds and formulations can be used on textiles, used as bio-barriers against microbial contamination, such as for fruit, vegetables, and plants, whether grown just above soil or on trees or harvested in green houses.

Other applications include Congregational and Sports Hygiene for correctional institutions; cruise lines convention centers; subways and terminals; airports and terminals theaters, buses; trains and planes, sport and fitness facilities, including but not limited to locker rooms, training rooms, pools, mats such as Yoga wrestling and wall mats, exercise balls basket balls, soccer balls, volleyballs: benches synthetic fields, team uniforms and team equipment. The above-described compounds and formulations compositions can be used on all interior and exterior applications of this type of congregational structure. The cruise and ship lines can use it as an anti-fouling coating. It can be applied for example to handrails, all textiles, carpets, seats furniture, outdoor furniture, umbrellas; trays, furnishing, and linens such as sheets and napkins. The same applications above can be used for hospitality inclusive of restaurants and hotels, The above-described compounds and formulations can also be used in the Food & Beverage industry. Possible applications include conveyor belts; interior and exterior surfaces, including walls, floors, ceilings; filters air-ducts systems; roofing and siding materials; refrigerators; cooling and heating systems; all holding tanks; hooks, carcasses; all materials used in packaging such as paper; cellophane; composite trays; tray napkins, all textiles, masks, gloves, uniforms, towels; wipes, hats foot gear, metallic processing tables, and industrial processing equipment; bins; trays; boxes corrugated or wood; hoses; beverage tanks; tubing; bottling and storage, disposable garbage bags, trucks and other transportation vehicles, and disposable wiping cloths that can be used for multiple purposes such as dusting or washing furniture, cars, walls, windows, floors, appliances, dishes, counter tops.

There are numerous applications in the military as well. Some examples are application to wound dressings, uniforms, socks, footgear; head gear; masks; underwear; gloves, outerwear; absorbents; sleeping bags; tents; mobile hospital textiles; trucks; helicopters; planes ambulances; and hospital settings as described above.

We claim:

1. A product made according to the steps of aerosolizing a microbiostatic agent, spraying said agent onto a substrate, said substrate having been acid treated to reach a neutral to acidic pH prior to contact with said microbiostatic agent, and allowing said microbiostatic agent to dry on and covalently bond to said substrate, said microbiostatic agent comprising a water-stable composition comprising:
   a) water;
   b) a product that is formed by reacting in water an organosilane, said organosilane optionally having a nonhydrolyzable organic group, but having one or more hydrolyzable groups;
   c) pentaerythritol;
   d) chloropropyltrimethoxysilane; and
   e) a non-ionic wetting agent selected from the group consisting of ethoxylated alcohol 9-12 moles ethoxylate, or ethoxylated alkyl phenol 9-12 moles ethoxylate.

2. The product of claim 1, wherein aerosolization is accomplished via an aerosolization apparatus utilizing ultrasonic energy to form 1 to 8 micron particles.

3. A product according to claim 1, wherein said substrate is a fabric selected from nonwoven fabric, woven fabric, nano fibers, microfibers, synthetic substrates, polymers, polypropylene; polystyrene; polyethylene rayon, and nitril.

4. A product according to claim 1, wherein said substrate is a solid surface.

5. A product according to claim 1, wherein said substrate is an organic surface.

6. A product according to claim 1, wherein the substrate is moving during application and is contained in a box with a heater.

7. The product of claim 2, wherein aerosolization is accomplished via an aerosolization apparatus utilizing ultrasonic energy to form 1 to 8 micron particles.

8. A product according to claim 2, wherein said substrate is a fabric selected from nonwoven fabric, woven fabric, nano fibers, microfibers, synthetic substrates, polymers, polypropylene; polystyrene; polyethylene, rayon, and nitril.

9. A product according to claim 2, wherein said substrate is a solid surface.

10. A product according to claim 2, wherein said substrate is an organic surface.

11. A product according to claim 2, wherein the substrate is moving during application and is contained in a box with a heater.

12. The product according to claim 1, wherein the substrate is a synthetic extruded polymer.

13. The product according to claim 2, wherein the substrate is a synthetic extruded polymer.

14. The product according to claim 12, wherein said synthetic extruded polymers are selected from polypropylene; polystyrene and nitril.

15. The product according to claim 12, wherein said synthetic extruded polymers are selected from polypropylene; polystyrene and nitril.

16. The product according to claim 1, comprising a medical filtration material.

17. The product according to claim 2, comprising a medical filtration material.

18. The product according to claim 1, comprising treated athletic gear, including but not limited to shoulder pads, helmets, shin guards, forearm guards, kidney protector pads; footwear; wrist guards, ankle guards yoga mats, wrestling mats, wall mats; fitness and workout mats, padding synthetic grass materials and backing comprised of but not limited to polypropylene blades, rubber and sand based filler materials.

19. The product according to claim 2, comprising treated athletic gear, including but not limited to shoulder pads, helmets, shin guards, forearm guards, kidney protector pads; footwear; wrist guards, ankle guards yoga mats, wrestling mats, wall mats; fitness and workout mats, padding synthetic grass materials and backing comprised of but not limited to polypropylene blades, rubber and sand based filler materials.

20. The product according to claim 1, wherein said substrate is a fabric covalently bonded to said microbiostatic agent and said a non-ionic wetting agent consists of tergitol NP-10.

21. The product according to claim 1, comprising a hand treating composition incorporated into a liquid solution comprising combination solutions of alcohols, aloe, or natural based oils.

22. The product according to claim 21, wherein said liquid is infused into a non-woven hand wipe material.

23. A product made according to the steps of exhausting a formulation for a microbiostatic agent comprising a water-stable composition comprising:
   a) water;
   b) a product that is formed by reacting in water an organosilane, said organosilane optionally having a nonhydrolyzable organic group, but having one or more hydrolyzable groups;
   c) pentaerythritol;
   d) chloropropyltrimethoxysilane; and
   e) a non-ionic wetting agent selected from the group consisting of ethoxylated alcohol 9-12 moles ethoxylate, or ethoxylated alkyl phenol 9-12 moles ethoxylate onto a substrate, said substrate having been acid-treated to reach a neutral to acidic pH prior to contact with said microbiostatic agent.

24. A product made according to the steps of wet padding onto textiles a formulation for a microbiostatic agent, said textile having been acid-treated to reach a neutral to acidic pH prior to contact with said microbiostatic agent, said formulation covalently bonding to said textile, and said formulation comprising a water-stable composition comprising:
   a) water;
   b) a product that is formed by reacting in water an organosilane, said organosilane optionally having a nonhydrolyzable organic group, but having one or more hydrolyzable groups;
   c) pentaerythritol;
   d) chloropropyltrimethoxysilane; and
   e) a non-ionic wetting agent selected from the group consisting of ethoxylated alcohol 9-12 moles ethoxylate, or ethoxylated alkyl phenol 9-12 moles ethoxylate.

25. The product of claim 23, wherein said water stable formulation consists of (trihydroxysilyl)propyldimethyloctadecyl ammonium chloride, chloropropyltrimethoxysilane and pentaerythritol, and said non-ionic wetting agent is ethoxylated nonyl phenol 10 moles EO.

26. The product of claim 24, wherein said water stable formulation consists of (trihydroxysilyl)propyldimethyloctadecyl ammonium chloride, chloropropyltrimethoxysilane and pentaerythritol, and said non-ionic wetting agent is ethoxylated nonyl phenol 10 moles EO.

27. The product according to claim 1, wherein said neutral to acidic pH is preferably from pH 6.0 to pH 4.5 and said acid used in treatment is selected from acetic and/or citric acids.

28. The product according to claim 23, wherein said neutral to acidic pH is preferably from pH 6.0 to pH 4.5 and said acid used in treatment is selected from acetic and/or citric acids.

29. The product according to claim 24, wherein said neutral to acidic pH is preferably from pH 6.0 to pH 4.5 and said acid used in treatment is selected from acetic and/or citric acids.

* * * * *